(12) United States Patent
Phillips et al.

(10) Patent No.: US 7,073,456 B2
(45) Date of Patent: Jul. 11, 2006

(54) METHOD FOR MANUFACTURING STENT-GRAFTS

(75) Inventors: Peter Phillips, Abingdon (GB); Adrian Michael Woodward, Nr. Royston (GB); Andrew Richard Buchanan Halket, Cherry Hinton (GB); Gail Beaton, Henley-on-Thamos (GB); Carl John Perks, Cambs (GB); Clive Graham Angel, Nr. Royston (GB); Timothy Faulkner Frost, Cambs (GB)

(73) Assignee: Anson Medical Limited (GB)

( * ) Notice: Subject to any disclaimer, the term of this patent is extended or adjusted under 35 U.S.C. 154(b) by 0 days.

(21) Appl. No.: 10/476,349

(22) PCT Filed: May 1, 2002

(86) PCT No.: PCT/GB02/01970

§ 371 (c)(1),
(2), (4) Date: Sep. 10, 2004

(87) PCT Pub. No.: WO02/087471

PCT Pub. Date: Nov. 7, 2002

(65) Prior Publication Data

US 2005/0013841 A1    Jan. 20, 2005

(30) Foreign Application Priority Data

May 1, 2001    (GB) .................................... 0110670.7

(51) Int. Cl.
*D05B 23/00*    (2006.01)
*A61B 17/062*    (2006.01)
(52) U.S. Cl. .................................. 112/475.17; 606/144
(58) Field of Classification Search ........... 112/475.17, 112/475.16, 475.26, 475.08, 157, 139, 470.12, 112/63, 470.29; 24/713.2, 714.2, 585.1; 623/1.15, 1.32, 23.64; 606/144–151
See application file for complete search history.

(56) References Cited

U.S. PATENT DOCUMENTS 3,316,870 A * 5/1967 Burbank ................. 112/475.16
3,600,767 A * 8/1971 Cowdrey et al. .............. 24/396

(Continued)

FOREIGN PATENT DOCUMENTS

DE    105 121 C    3/1898

(Continued)

*Primary Examiner*—Ismael Izaguirre
(74) *Attorney, Agent, or Firm*—Craig A. Fieschko, Esq.; DeWitt Ross & Stevens S.C.

(57) ABSTRACT

A sewing machine is provided which is capable of sewing reinforcing wire to tubular grafts in order to form stent grafts. A bobbin (which may be seated in a shuttle) carries a bottom thread through the bore of the tubular graft and forms a stitch in combination with a top thread carried on a needle which pierces the graft wall.

25 Claims, 5 Drawing Sheets

U.S. PATENT DOCUMENTS

| | | | |
|---|---|---|---|
| 3,714,671 A * | 2/1973 | Edwards et al. | 623/2.19 |
| 4,080,915 A | 3/1978 | Bompard et al. | |
| 4,502,159 A * | 3/1985 | Woodroof et al. | 623/1.41 |
| 5,226,379 A * | 7/1993 | Everett | 112/475.26 |
| 5,755,727 A * | 5/1998 | Kontos | 606/144 |
| 5,925,076 A | 7/1999 | Inoue | |
| 6,178,903 B1 | 1/2001 | Kaetterhenry et al. | |
| 6,334,867 B1 | 1/2002 | Anson | |
| 6,432,134 B1 | 8/2002 | Anson et al. | |

FOREIGN PATENT DOCUMENTS

| | | |
|---|---|---|
| DE | 26 28 340 A | 1/1977 |
| DE | 38 24 007 A | 1/1990 |
| WO | WO 99 37242 A | 7/1999 |
| WO | WO 01 30269 A | 5/2001 |

* cited by examiner

METHOD FOR MANUFACTURING STENT-GRAFTS

FIELD OF THE INVENTION

This application relates to a sewing machine and in particular to a sewing machine for use in the construction of vascular stent-grafts.

BACKGROUND OF THE INVENTION

Stent-grafts are tubular constructions for use inside blood vessels. They generally comprise two components: a quasi blood-tight tube that is usually formed of textile or membranous material, and a reinforcing structure which is usually made of wire or other filamentous metallic material.

The tubular graft component is usually made from woven polyester fabric, although a few designs employ PTFE membranes. The graft is supported on metallic rings which are generally formed from wire but are occasionally cut from metal tube by means of laser cutting or similar means. When attached to the graft, the metal rings can define a single plane at an angle to the axis of the graft, the rings can be corrugated so that they define the surface of a short cylinder on the surface of the graft, or the rings can be fenestrated or linked so as to produce a long cylindrical reinforcing element on the surface of the graft.

In almost all designs, the reinforcing rings are attached to the surface of the graft by means of sutures which are generally applied by hand. Some designs employ many hundreds or thousands of sutures and the time and cost associated with attaching these sutures is high. Additionally, the burden of assuring the quality of every stitch is expensive, while the implications of poor quality stitching in a device which is implanted into a patient can be particularly serious to the health of the patient.

There is also a requirement to manufacture stent-grafts to fit the anatomies of individual patients. In particular, the lengths, diameters, tapers, secondary tapers and the location of side-branches of stent-grafts are required to be tailor-made for each patient and this can take an unfeasible period of time when the stent-graft is made by hand.

An alternative solution has been described in WO 99/37242 (in the name of the present applicant) in which computerised embroidery is used to manufacture a flat-form device which is subsequently rolled into a tube. This approach solves many of the issues associated with hand manufacturing but results in a seam and prevent some continuous structures from being designed.

GB 2165559 (University College London) discloses a sewing machine for forming stitches in a substrate, for example body tissue, during surgery. The sewing machine employs suction to pull a folded section of the substrate into the machine so that it is disposed between a needle and a hook. The needle can then be used to feed thread through the folded section of substrate to emerge the other side, and to engage the thread on the hook. This action is repeated with the sewing machine being moved along the substrate, thereby forming stitches in the substrate. This sewing machine could not be employed to stitch thread to the wall of a tubular graft, because the graft would not be sufficiently compliant to enable a folded section of graft to be sucked into the machine.

U.S. Pat. No. 4,502,159 (Shiley Incorporated) discloses a method for forming a tubular prosthesis by rolling pericardial tissue into a tube and stitching along the tube to form a longitudinal seam. However, the stitches are formed conventionally by passing a thread from one side of the seam to the other on the outside of the tube.

U.S. Pat. No. 4,241,681 (Porter) discloses a sewing machine for sewing a series of spaced reinforcing rings on a long flexible tube of fireproof fabric. The machine comprises, a long tubular support over which the work piece is pulled like a sleeve on an arm. A fixed stitching mechanism is provided for forming chain stitch in the work piece, and a puller mechanism advances the work piece over the support as the stitches are formed therein.

U.S. Pat. No. 4,414,908 (Janome Sewing Machine Co., Limited) discloses a suturing machine for suturing incised parts of a patient. The machine comprises a needle holder (effectively a pair of pliers) and a shuttle holder which is slideably mounted on the needle holder. This means that movement of the needle independently of the shuttle is not possible for all degrees of freedom. In particular, movement of the needle holder to pierce the needle through the wall of a tubular implant would inevitably result in a corresponding movement of the shuttle within the bore of the implant. In practice, it would not be possible to manipulate the needle without causing the shuttle to impact the side walls of the implant, thereby risking damage to the implant.

In an alternative embodiment of U.S. Pat. No. 4,414,908, the shuttle is mounted on a rod which is slideable parallel to the longitudinal axis of the needle holder and the needle holder is rotatable circumferentially about the axis of the shuttle rod. This means that rotation of the needle holder causes the needle to follow a circumferential path which is a constant distance from the shuttle. Thus the needle could never penetrate the side wall of a tubular implant. Rather, it would simply circle around the implant, keeping a constant distance from the centre of the bore.

SUMMARY OF THE INVENTION

The present invention is designed to address the above-mentioned short-comings by allowing the reinforcing rings to be attached by sutures which are applied with a sewing machine which is controlled by computer. The sewing machine comprises a number of novel mechanisms which permit sewing onto the surface of narrow tubes and the stitching of wires or other structures onto the surface of the tube. Specifically, structures can be sewn to the inner or outer surfaces of the tube.

The machine described herein can also be used to manufacture other tubular devices which incorporate a filamentous component in which the filamentous component is applied to the surface of the tube in a separate operation to the formation of the tube itself.

WO 01/30269 (in the name of the present applicant) was published after the priority date of the present application. It relates to a method and apparatus for stitching thread to the wall of a graft, for example to form a graft-stent. The present invention is an improvement thereto.

According to a first aspect of the present invention, there is provided apparatus for stitching thread to the wall of a tubular medical implant, comprising a support for the implant, a needle to drive a first thread through the wall and into the bore of the implant, and a bobbin for carrying a second thread through an open end of the implant into said bore in order to form a stitch in combination with the first thread.

The needle and the bobbin are preferably disposed so that the longitudinal axes thereof lie in a common plane. Preferably, the axes are at 90°.

The relative positioning of the needle and the bobbin allows the stitches to be made in a more confined environment than is possible with a conventional sewing machine, thereby allowing stitches to be made in the wall of relatively small diameter tubular grafts.

According to a second aspect of the present invention, there is provided apparatus for stitching thread to the wall of a tubular medical implant, comprising a support for the implant, a needle to drive a first thread through the wall and into the bore of the implant, and a bobbin for carrying a second thread through an open end of the implant into said bore in order to form a stitch in combination with the first thread, wherein an elongate bobbin support is provided to support the bobbin inside the bore of the implant.

In a preferred embodiment, the bobbin support is a rod having a recess in which the bobbin can be seated.

In an alternative embodiment, the bobbin support is a runner in which the bobbin is free to move into and out of said bore. Preferably, the runner is in the form of a tube with a slot provided therein to allow the needle access to the bobbin through the slot.

In a particularly preferred embodiment, the bobbin sits in a shuttle which itself either sits in the recess in the rod or is able to move up and down the runner.

Preferably, the shuttle is biased towards the side of the runner proximate the path of the needle so that in use the shuttle is positioned to engage the loop of the first thread, the biasing being such as to allow movement of the shuttle away from the bias to a sufficient extent to allow the second thread to be wound on and off the shuttle.

In a further embodiment, at least one end of the shuttle is narrowed and optionally curved so that when its orientation is maintained in the runner as described above, the tip of the shuttle is brought close to the tip of the needle and the centre of the loop of suture.

The embodiment in which the bobbin sits in a runner is particularly suitable for small diameter grafts (perhaps from 3 to 6 mm), whereas the embodiment in which the bobbin is seated in a recess in a rod is suitable for grafts having a larger diameter (perhaps from 7 to 40 mm).

In a preferred embodiment, friction is applied to the second thread by weaving it through a series of holes in the shuttle or bobbin carrier, the greater the number of holes, the greater the braking effect.

In one embodiment, said apparatus additionally comprises means for tensioning said second thread to facilitate the formation of stitches. The means for tensioning may comprise a trapping body adapted to move along the runner independently of the shuttle and a stop on the opposite side of the shuttle to the trapping body, the arrangement being such that in use the second thread passes between the trapping body and the shuttle as it leaves the shuttle and can be trapped between the trapping body and the shuttle by urging the trapping body into the shuttle against the stop, in order to allow tension to be applied to the second thread when forming a stitch.

In an alternative embodiment, the means for tensioning the second thread comprises resilient metal (such as a leaf spring) to trap the thread. The apparatus may comprise means for applying additional pressure to the resilient metal in order to facilitate the tensioning of the thread; said means may have the additional function of moving the shuttle along the runner. Thus the travel of the shuttle can be practically achieved by means of push rods which act on it at either end of the guide tube.

In a further embodiment, the apparatus may comprise a variable brake on the bobbin in the form of a screw acting on the bobbin, preferably via an 'O' ring rubber washer.

A yet further embodiment comprises a shuttle or bobbin carrier which can be rolled in order that the second thread has lie to across the surface thereof to increase the friction acting on the second thread and thereby have a braking effect.

In one embodiment, the manufacturing machine here described forms a two threaded lock stitch by means of a bobbin-carrier (and the mechanism) which is able to pass through the lumen of the tube being manufactured. During manufacture, a guiding tube passes through the entire length of the stent-graft and projects at either end of it. The guiding tube possesses a slit (which may be along its entire length) through which the needle passes to gain access to the shuttle. The needle carries, at its tip, a loop of suture material (or any thread), both free ends of which remain on the outer surface of the stent-graft. Ideally, the guide tube has a non-circular cross section so as to provide rigidity which has been lost as a result of forming the longitudinal slit.

The guide tube may be formed from at least one shaped strip of material which retains the shuttle by gravitational, magnetic or other near constant-force action. A second strip of material may form the tube in conjunction with the first.

According to a third aspect of the present invention, there is provided apparatus for stitching thread to the wall of a tubular medical implant, comprising a support for the implant, a needle to drive a first thread through the wall and into the bore of the implant, and a bobbin for carrying a second thread through an open end of the implant into said bore in order to form a stitch in combination with the first thread, the bobbin being mounted in a shuttle, wherein the shuttle is an elongate element with a D-shaped cross section for at least part of its length.

Preferably, the needle passes between the implant wall and the substantially planar longitudinal surface of the shuttle.

The shuttle preferably comprises a bobbin within a bobbin-carrier which is shaped approximately like a long, narrow cylinder. Ideally, the bobbin-carrier is not quite circular in cross section but has a feature, preferably a flattened surface, which can register against a corresponding feature in the guide tube, thereby maintaining the orientation of the bobbin-carrier about its long axis.

The needle is preferably shaped so as to be substantially straight with a section removed (a "scarf") to facilitate the formation of a loop. There may be a corresponding section "removed" from the shuttle in order that the needle and the shuttle fit together to enable them to occupy less room inside the bore of the graft than in a conventional sewing machine.

An unusual requirement when sewing stent-grafts is that structures should be able to be attached to each other only with the strength of a stitch. This is achieved in the current machine by independent control of the tension of threads in the bobbin and needle. Control of the bobbin thread has been described above and control of the needle thread is achieved by means of an electronically controlled tensioner which operates independently of the position of the needle.

According to a fourth aspect of the present invention, there is provided apparatus for stitching thread to the wall of a tubular medical implant, comprising a support for the implant, a needle to drive a first thread through the wall and into the bore of the implant, and a bobbin for carrying a second thread through an open end of the implant into said bore in order to form a stitch in combination with the first thread, and means for tensioning the first thread, wherein the means for tensioning operates independently of the mechanism for driving the needle.

A strain gauge may be provided in the path of the first thread, the second thread or both.

The stent-graft manufacturing machine requires a mechanism to hold the tubular stent-graft while reinforcements are stitched to its surface. Stent-grafts can have cylindrical sections and conical sections in them and along the length of an implant the rate of change of the diameter of the implant can have a number of different values. Stent-grafts may also be branched.

In order that the surface of the stent-graft is presented to the sewing head in a constant fashion, the machine incorporates a pair of attachment means which grip the stent-graft at its either ends in a way that allows the graft to be tensioned along its axis, to be translated along its axis and to be rotated about its axis. Additionally, the graft and attachment means can be rotated about a point or points on the surface of the graft so that the wall of the graft being stitched is retained at a constant distance and/or angle from the sewing head.

According to a fifth aspect of the present invention, there is provided a method for stitching thread to the wall of a tubular medical implant, comprising the steps of driving a first thread through the wall and into the bore of the implant using a needle, forming a loop of the first thread, moving a bobbin carrying a second thread through an open end of the implant into said bore, passing the second thread through the loop formed in the first thread, closing said loop in order to form a stitch, and withdrawing the bobbin from said bore.

In a preferred embodiment, the needle and the bobbin are disposed so that the longitudinal axes thereof lie in a common plane, and the needle is withdrawn sufficiently (preferably entirely) before the second thread is passed through the loop formed in the first thread in order that the bobbin does not contact the needle.

In a particularly preferred embodiment the following novel sequence of movements of the bobbin-carrier and needle are employed:

The needle passes through the wall of the stent-graft and approaches the opposite wall of the guide tube within the stent-graft.

The needle is partially withdrawn.

The shuttle is advanced until the tip of its nose engages the loop of suture.

The shuttle can be stopped at this point.

The needle is withdrawn further and can be pulled through the wall of the stent-graft.

The shuttle is advanced through the loop of suture. If insufficient thread is present, the shape of the nose of the shuttle will draw more needle thread through the wall of the stent-graft and into the guide tube to permit the shuttle to pass completely through the loop.

In a sixth aspect of the present invention, therefore, there is provided a method for stitching thread to the wall of a tubular medical implant, comprising the steps of driving a first thread through the wall and into the bore of the implant using a needle, forming a loop of the first thread, moving a bobbin carrying a second thread through the loop formed in the first thread, closing said loop in order to form a stitch, wherein said loop is formed in the first thread by beginning to withdraw the needle, but wherein the end of the needle is withdrawn completely from the bore only after the shuttle has engaged said loop.

The advantage of this method is that the sequential deployment of the bobbin and the needle enables the thread formation to take place in a restricted volume compared to prior art methods (which require that the needle and bobbin are adjacent simultaneously).

The first thread may be clamped whilst the stitch is being formed in order to create sufficient tension to unwind the second thread from the shuttle.

The mechanism driving the needle is also novel and is able to control the position of the needle at any instant to allow control of the needle independent of the bobbin. Conventional sewing machines employ a cam mechanism which links the movement of the bobbin to that of the needle and requires that the movements of each component be smooth and continuous. As described in the above sequence, the needle and bobbin of the present invention are controllable independently and continuous movement is not a requirement.

In a seventh aspect of the present invention, there is provided a method for stitching thread to the wall of a tubular medical implant having a straight section with substantially parallel walls and at least one tapered section with tapered walls, comprising the steps of driving a first thread through the wall and into the bore of the implant using a needle, forming a loop of the first thread, moving a bobbin carrying a second thread through an open end of the implant into said bore and passing the second thread through the loop formed in the first thread, closing said loop in order to form a stitch, and withdrawing the bobbin from said bore, wherein the implant is tilted in order that the axis along which the bobbin travels is substantially parallel to the wall in which the stitch is to be formed.

In order to aid the placement of features onto the surface of the implant a number of wire or reinforcement handling features can be added:

According to an eighth aspect of the present invention, there is provided a method for attaching reinforcement wire to the surface of a medical implant, comprising the steps of determining the position at which the wire is to be attached, locating the wire proximate said position, employing a needle to move the wire closer to said position, and employing said needle to make a stitch in the surface.

The needle is preferably positioned on the side of the wire opposite to the position at which the wire is to be attached with the tip of the needle disposed between the plane of the surface and the plane of the tangent of the wire parallel to the plane of the surface, moved towards said position such that it contacts the wire and moves it closer to said position, and moved substantially perpendicular to the surface to make a stitch therein.

The method steps are then repeated and the needle is employed in the second cycle to move the wire closer to the stitch formed in the first cycle, the thread passing over the wire from the first to the second stitch thereby attaching the wire to the surface close to or at the said position.

The apparatus preferably comprises means for determining the level of the graft surface and controlling the height of the needle relative to said level. This may simply be open loop control software which references the graft surface, although means for sensing the surface of the graft may be provided, with feedback software being provided to control the height of the needle.

This allows precise positioning of the wire on the surface of, for example, the tubular graft, the positioning step being incorporated into the sewing steps so result in an efficient and speedy process. It also restores the wire to its true shape, avoids the need for sensing exactly where the wire is, and avoids the situation in which the needle strikes the wire and is damaged.

In a preferred embodiment, the method includes the step of deforming the wire in order to attach wire in a predetermined configuration to the graft without the need for having pre-formed the wire into that configuration.

According to a ninth aspect of the present invention, there is provided apparatus for attaching reinforcing (or other) filament to a tubular medical implant, comprising a support for the implant, a needle to drive a first thread through the wall and into the bore of the implant, and a shuttle for carrying a second thread through an open end of the implant into said bore in order to form a stitch in combination with the first thread to attach the reinforcing filament to the implant wall, wherein the apparatus additionally comprises a support (such as a table) for the reinforcing filament, the support being moveable relative to the implant to enable the reinforcing filament to be positioned on the implant (preferably under tension) prior to attachment to the implant.

In one embodiment of a stent-graft, the wire reinforcing rings are formed from a continuous piece of wire which is formed into a flat, zig-zag pattern. In order to apply the wire to the stent-graft it is held on a moving tray which contains a belt feed mechanism. The feeder pushes the wire zig-zag down the tray to correspond with the wire being, attached along the length of the implant. The tray translates from side to side to allow the wire to be fed around the circumference of the stent-graft. By means of this mechanism, a stent-graft can be assembled automatically from the component parts of a graft tube and a pre-formed wire reinforcement.

According to an tenth aspect of the present invention, there is provided apparatus for shaping a length of reinforcing wire formed from a shape memory alloy prior to attachment of the wire to a medical implant, comprising means for holding and dispensing the wire, and means for laying the wire in the required pattern on the implant, wherein the apparatus additionally comprises means for localised heating of the wire in order to fix the wire into the required pattern prior to attachment to the implant.

An improvement on the above system which allows a wider range of stent-grafts to be manufactured automatically includes a mechanism to make the appropriate bends in wire just prior to its attachment to the surface of the stent-graft. Such a mechanism comprises a spool of wire and feed mechanism and at least one pair of jaws which incorporate the desired radius of bend or can be used together to form the desired radius of bend. When the jaws grasp the wire and heat is applied, the wire will adopt a 'set' as defined by the radius of curvature of the jaws or the way in which the pairs of jaws are positioned with respect to one another. Conveniently, heat can be applied by passing an electrical current through the wire or by heating the jaws directly, although other means are well known. Ideally, the jaws can be made of an engineering ceramic material which will have the strength to form the wire and resist heat but the insulating properties required to be able to pass an electric current through the wire.

Some other structures which are applied to the surface of stent-grafts also require forming but do not require heat or high forces to achieve the necessary 'set'. An example of such a structure is a radio-opaque marker which can be made of a metal with a high atomic number or from a polymer which incorporates metals or salts with a similar atomic number. One suitable metal is tantalum, which is highly malleable.

In an eleventh aspect of the present invention, therefore, there is provided apparatus for attaching wire (preferably a marker wire) to the wall of a tubular medical implant circumferentially around the implant and longitudinally along the implant, comprising a support for the implant, a needle to drive a first thread through the wall and into the bore of the implant, a bobbin for carrying a second thread through an open end of the implant into said bore in order to form a stitch in combination with the first thread to attach the wire to the implant wall, and a tube through which the wire is fed in order to be placed on the implant in the correct position prior to attachment to the implant, wherein the said tube is adapted to move from a first position in which it is perpendicular to the longitudinal axis of the implant to a second position in which it is parallel to said axis, to facilitate positioning of the wire on the implant. Preferably, the tube can be positioned to feed wire adjacent to the needle from any direction around the axis of the needle. Pinch rollers may be provided to feed said wire down said tube.

The machine described advantageously incorporates a spool of tantalum wire or similar filamentous material of appropriate radio-opacity and a guiding orifice or tube. The orientation of the guiding orifice or tube is controlled by computer so that depending upon the movement of the stent-graft (i.e. whether rotating or translating about its axis) the filamentous material can be fed out under the sewing head along the line of movement of the surface of the stent-graft. As a result of the malleable nature of the filamentous material, it can be so arranged to lie circumferentially about the stent-graft or in parallel with its axis.

With improvement, the mechanism can be adapted to wrap wires spirally along the body of the stent-graft and this can permit other designs of reinforcement means to be attached or for other patterns of filamentous structure to be attached to the surface of the implant.

BRIEF DESCRIPTION OF THE DRAWINGS

A number of preferred embodiments of the present invention will now be described with reference to the accompanying drawings, in which:—

DETAILED DESCRIPTION OF PREFERRED EMBODIMENTS OF THE INVENTION

Figure 1:
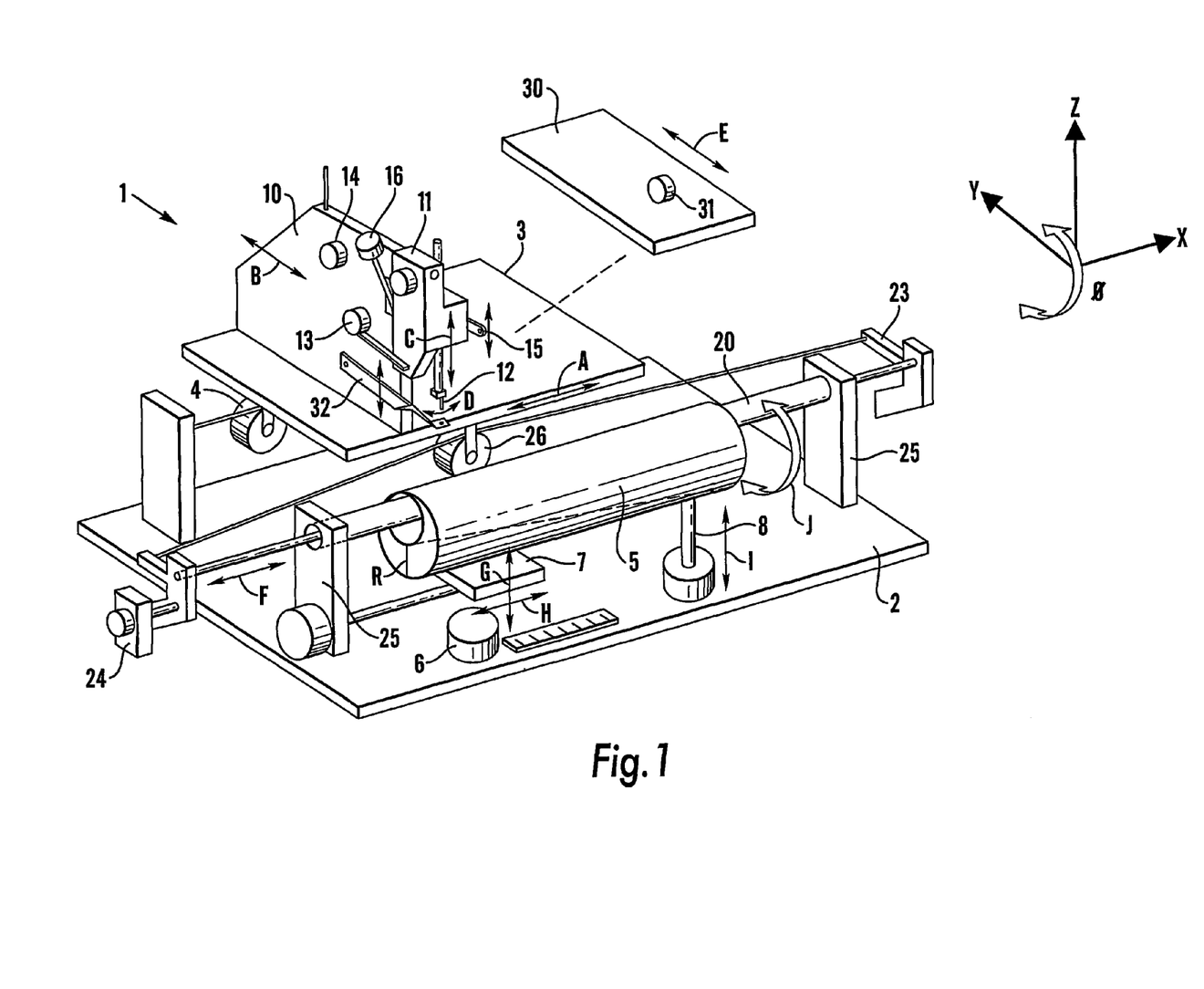
FIG. 1 is a schematic depiction, in perspective, of apparatus in accordance with the invention.

Turning to FIG. 1, sewing machine 1 comprises a base 2 having mounted thereon a sew arm 10, shuttle tube 20 and stent table 30.

Graft 5 is held by a pair of grips (not shown) at either end of graft 5 with shuttle tube 20 passing through the lumen of graft 5 and being supported at either end by shuttle tube supports 25 which are also mounted on base 2.

Sew arm 10 is mounted on carriage 3 which is driven by carriage drive 4 in directions parallel and perpendicular to shuttle tube 20 (as indicated by arrows A and B respectively) so that sew arm 10 can be positioned as required relative to graft 5.

Sew arm 10 comprises a needle head 11 which projects over the edge of carriage 3 and which has needle 12 which can be driven up and down relative to graft 5 (as indicated by arrow C) and side to side (so-called "needle wobble") by needle wobble drive (as indicated by arrow D). Needle head 11 controls the deployment of the top thread (not shown), which passes from a spool (not shown) to stitch maker 15 (controlled by stitch maker motor 16), though the eye of needle 12 and then engages with top thread tensioner 14.

The wire which is used to form the stent on the surface of graft 5 is laid pre-formed on stent table 30, which is driven into position relative to graft 5 by stent table drive 31 in the direction shown by arrow E. The wire (not shown) is retained in position whilst being sewn to graft 5 by wire guide 32 which is attached to sew arm 10.

Figure 2:
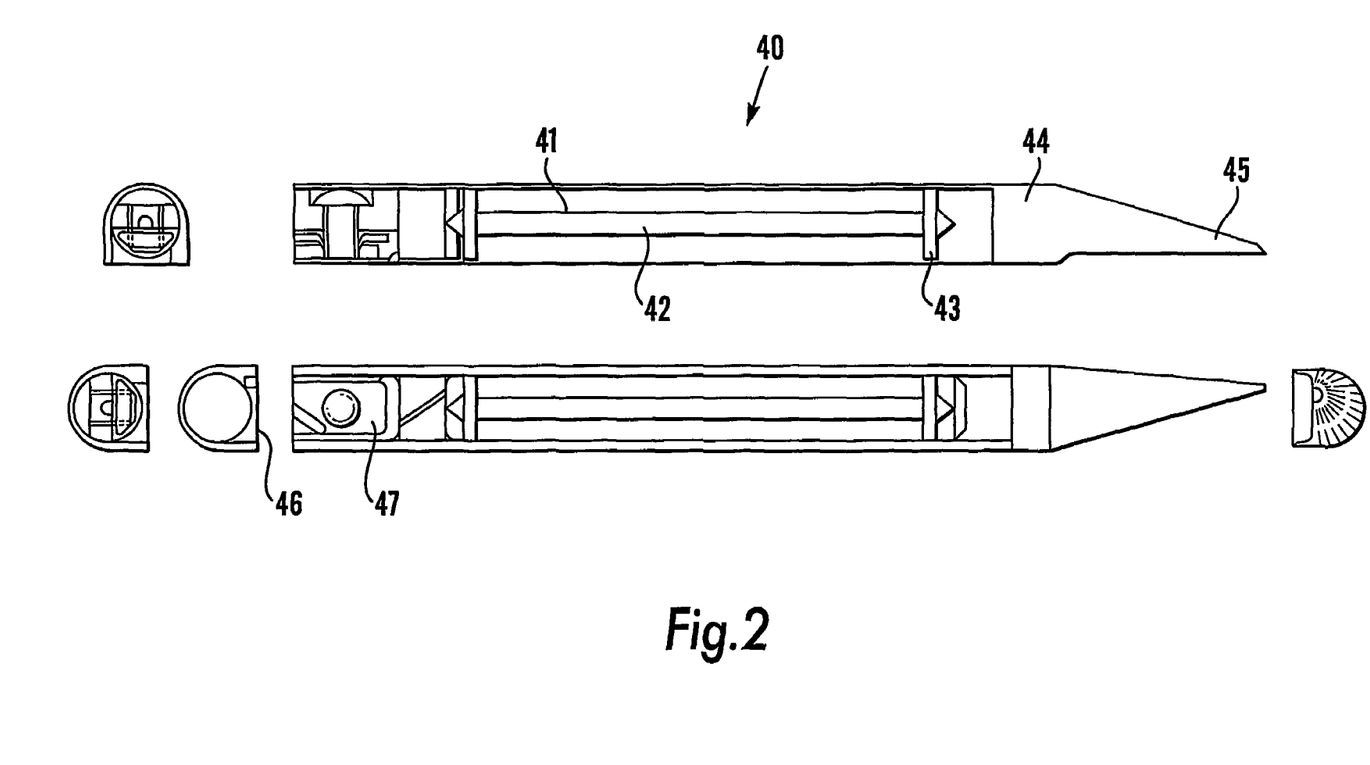
FIG. 2 is a side view in partial cross-section of a shuttle in accordance with the invention.
Figure 3:
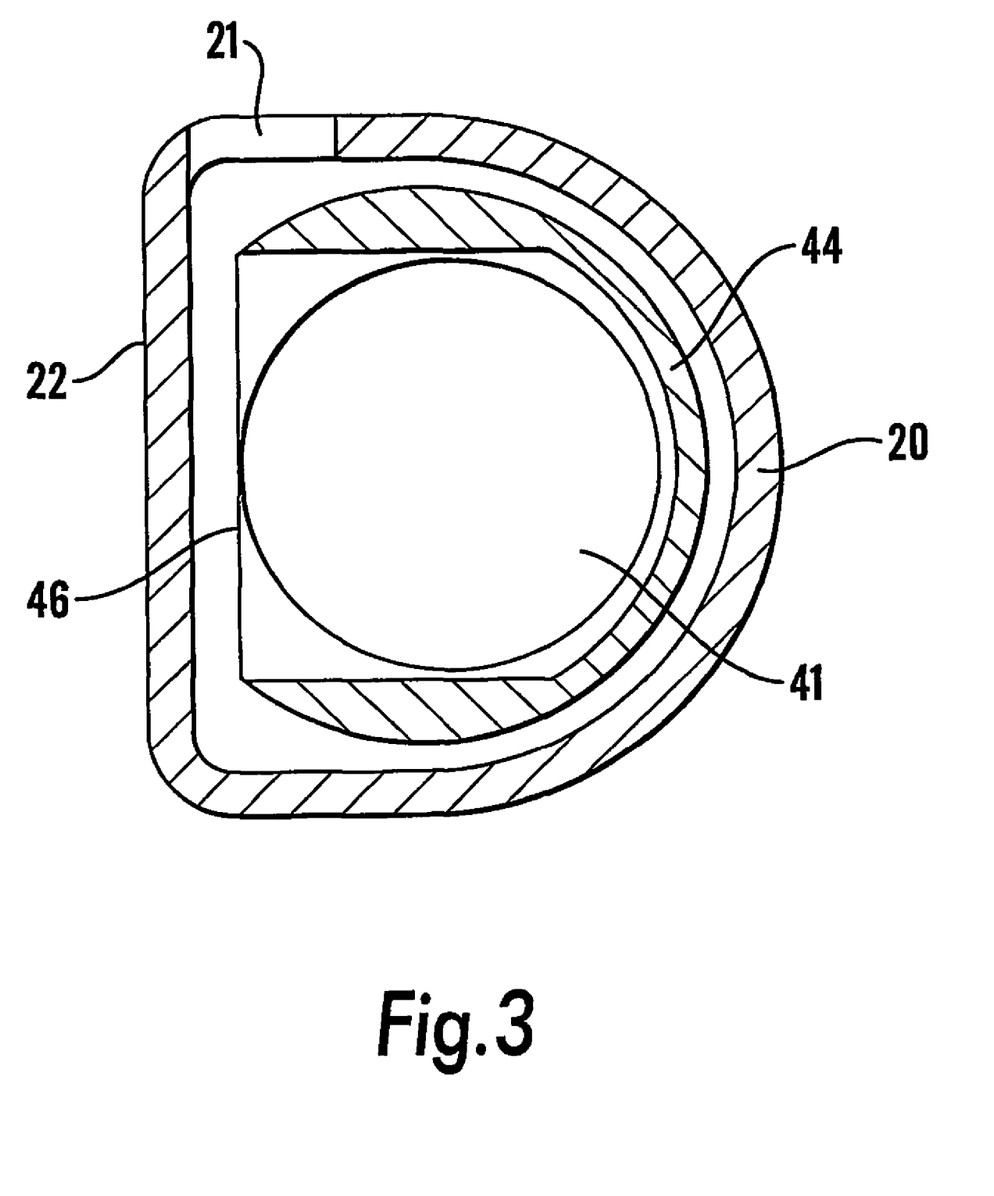
FIG. 3 is an end view in partial cross-section of an alternative embodiment of the shuttle of FIG. 2 in the guide tube of FIG. 1.

Turning to FIGS. 2 and 3, shuttle 40 comprises a bobbin 41 for carrying the bottom thread (not shown) and a bobbin carrier 44 for bobbin 41. Bobbin 41 is in the form of an elongate spool with a narrowed central axis 42 around which the bottom thread can be wound and end rollers 43 about which bobbin 41 can roll so that the thread can unwind from axis 42. Bobbin 41 sits loosely in the central cavity of bobbin carrier 44 to enable thread to be unspooled easily from bobbin 41.

Bobbin carrier 44 is elongate in shape and has asymmetric nose 45 which is displaced laterally from the longitudinal axis of bobbin carrier 44 so as to engage a loop of top thread as will be described below. The body of bobbin carrier 44 (that part distinct from nose 45) has parallel top and bottom walls connected by a flat side wall 46 and a curved side wall opposite to side wall 46. This shape mirrors the shape of the internal cavity of shuttle tube 20, so that shuttle 40 can be seated loosely in shuttle tube 20 with flat side wall 46 substantially parallel to flat side wall 22 of shuttle tube 20. In this manner, shuttle 40 can be moved longitudinally back and forth along shuttle tube 20 but is prevented from rotating about its longitudinal axis because side wall 46 is longer than the notional internal diameter of the curved section of shuttle tube 20.

It will be noted that FIGS. 2 and 3 depict slightly different embodiments, in that the external profile of bobbin carrier 44 differs somewhat. However, the function is unaltered, and in particular wall 46 acts in both cases to prevent bobbin carrier 44 from rotating in shuttle tube 20.

FIG. 3 also depicts slot 21 in shuttle tube 20, through which needle 12 passes during the sewing process (described below).

Figures 4A, 4B, 4C:
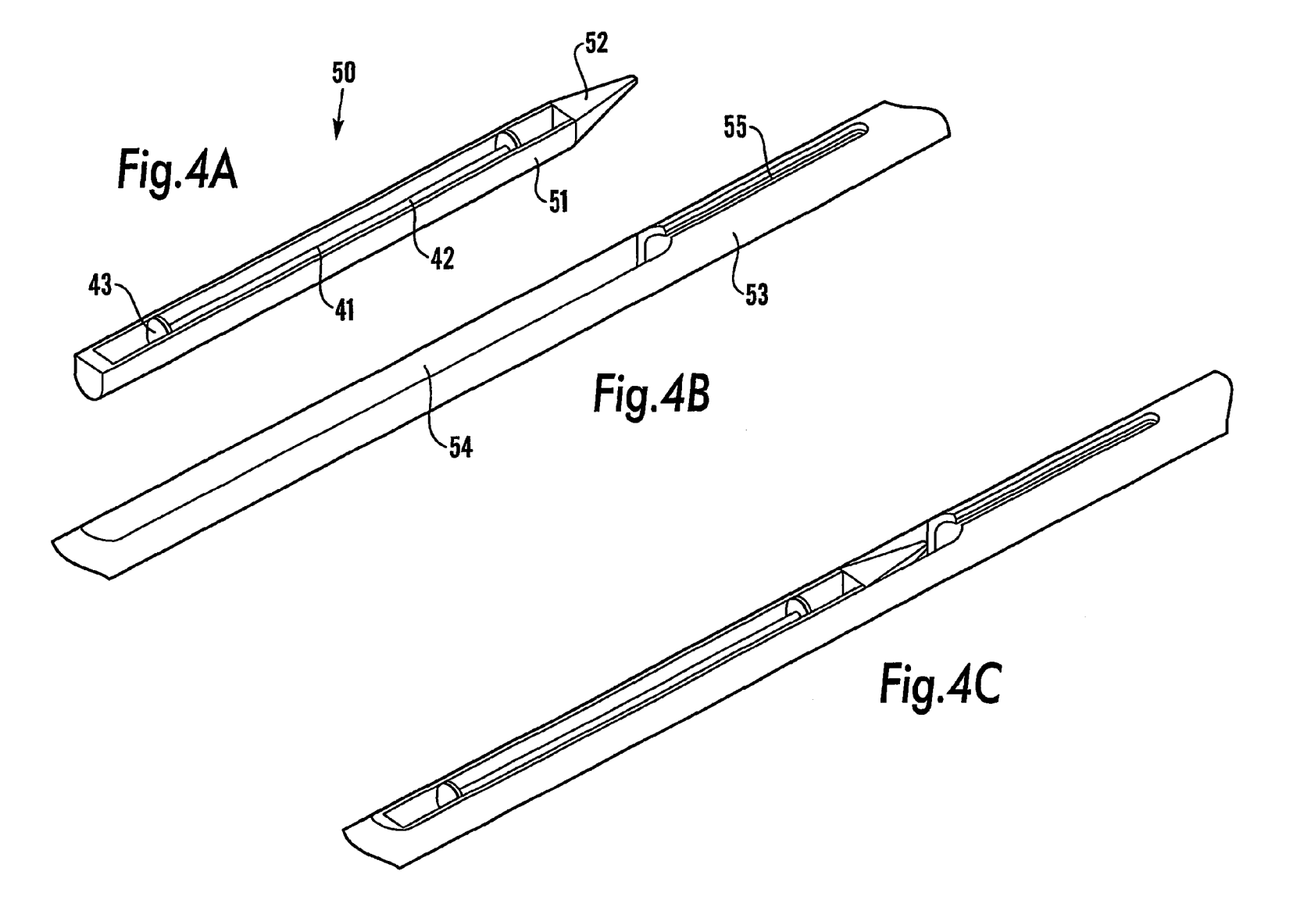
FIG. 4A is a perspective view of an alternative embodiment of a shuttle in accordance with the invention.
FIG. 4B is a perspective view of a shuttle support in accordance with the invention.
FIG. 4C is a perspective view of the shuttle of FIG. 4A seated in the shuttle support of FIG. 4B.
Figure 5A:
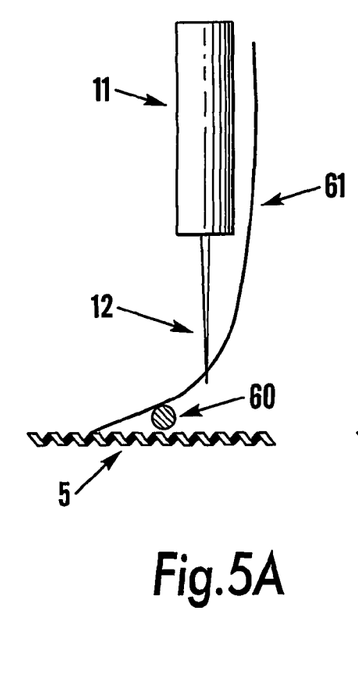
FIGS. 5A to 5D depict schematically the operation of the apparatus in accordance with the invention to attach wire to the surface of a graft.
Figure 5B:
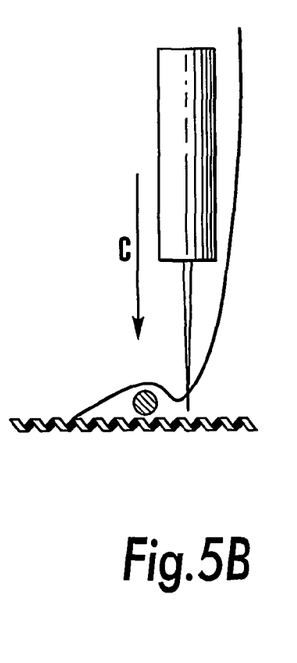
Figure 5C:
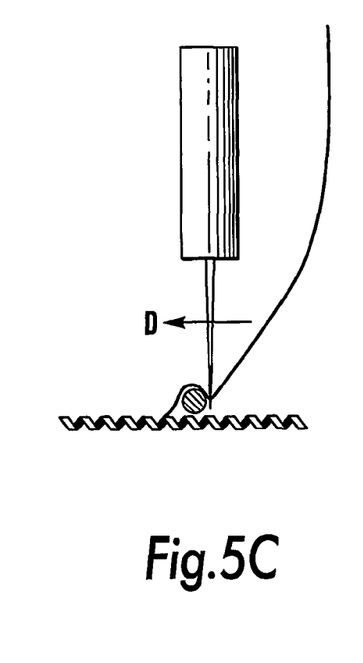
Figure 5D:
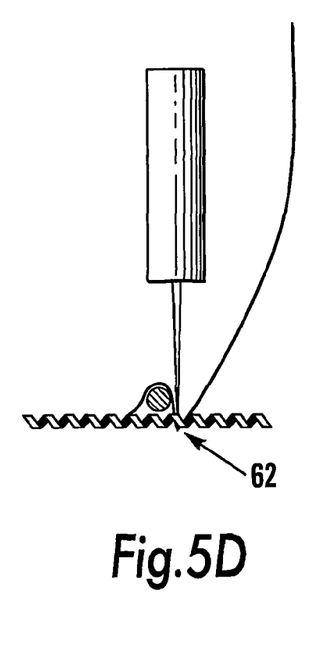

FIG. 4A depicts an alternative embodiment of a shuttle 50 comprising bobbin 41 with central axis 42 and end rollers 43 as described above, and bobbin carrier 51 which is formed substantially similarly to bobbin carrier 44 described above except that the nose 52 of bobbin carrier 51 is symmetrical in shape about the vertical plane containing its longitudinal axis.

FIG. 4C shows shuttle 50 seated in recess 54 of shuttle rod 53, which is shown on its own in FIG. 4B. Shuttle rod 53 also has slit 55 therein, disposed in a vertical plane containing its longitudinal axis.

Returning to FIG. 1, shuttle drive motor 26 operates to drive shuttle drive arms 23 into and out of either end of shuttle tube 20 in the direction of arrow F so as to move shuttle 40 backwards and forwards along shuttle tube 20.

Shuttle thread tensioner 24 operates to tension the bottom thread on bobbin 41 by increasing the pressure on a leaf spring 47 so as to trap the bottom thread under leaf spring 47, thereby enabling tension to be applied.

The position of graft 5 relative to shuttle tube 20 can be adjusted by means of graft bed height drive 6, which moves graft bed 7 (on which graft 5 rests) up and down relative to shuttle tube 20 (in the direction of arrow G) and from side to side parallel to the longitudinal axis of shuttle tube 20 (in the direction of arrow H).

If it is necessary to tilt graft 5 (for example when sewing on the surface of a tapered position) then this can be done by means of graft tilt drive 8, which raises and lowers one end of graft 5 in the direction shown by arrow I. Graft 5 is rotated about its longitudinal axis (in the direction of arrow J) by rotation of the graft grip at either end.

The operation of sewing machine 1 will now be described with reference to FIGS. 1 to 3.

Graft 5 is placed over shuttle tube 20 by disengaging shuttle tube 20 from shuttle tube support 25 and passing graft 5 over shuttle tube 20 so that shuttle tube 20 passes through the lumen of graft 5. The graft grips (not shown) are then operated to engage either end of graft 5 and graft 5 is positioned correctly with respect to needle head 11 by operation of graft bed height drive 6 and graft tilt drive 8. Rotation of graft 5 about its longitudinal axis takes place to ensure that the surface of graft 5 to which a support wire is to be sewn is facing upwards away from base 2.

The support wire for forming the stent on graft 5 is pre-formed on stent table 30, which is positioned over the surface of graft 5 by operating stent table drive 31. The support wire is held in place over graft 5 by wire guide 32 on sew arm 10, which is in turn driven into place over graft 5 by operation of carriage drive 4 to drive carriage 3.

The above process locates the support wire approximately into position with respect to graft 5. The support wire may be accurately positioned by operating needle wobble drive as will be described below with reference to FIGS. 5A to 5D:

Needle 12, which carries the top thread 61, is first positioned close to support wire 60 and then lowered (arrow C) to be just above the surface of graft 5. Needle 12 is then moved sideways (arrow D) by needle wobble drive to push wire 60 close to the previous stitch. Needle 12 is then driven downwardly through the wall of graft 5 at position 62 close to wire 60.

Once needle 12 has fully pierced the wall of graft 5 it passes through slot 21 in shuttle tube 20 so that the end of needle 12 is positioned towards the end of side wall distal from slot 21. Needle 12 is then partially withdrawn so that the friction between the top thread and the wall of graft 5 causes the creation of a loop in the top thread within shuttle tube 20.

Shuttle drive motor 26 now operates on shuttle drive arm 23 to drive shuttle 40 down shuttle tube 20 into the lumen of graft 5 with asymmetric nose 45 of bobbin carrier 44 in front. As shuttle 40 is advanced towards the loop of top thread, nose 45 engages the loop, aided by the asymmetric positioning of nose 45 towards flat side wall 46 of bobbin carrier 44. The bottom thread, which is wound around central axis 42 of bobbin 41, trails behind shuttle 40.

Once shuttle 40 has engaged the loop of top thread its movement is halted and needle 12 is withdrawn completely from the wall of graft 5, leaving behind a loop of the top thread. Shuttle 40 is then advanced so that it passes completely through the loop of top thread and emerges on the other side.

A stitch is now formed by passing the bottom thread over the top thread. This is achieved by the combined action of top thread tensioner 14 and stitch maker 15 which is driven by stitch maker motor 16 upwardly away from graft 5 thereby closing the loop in the top thread. At the same time, top thread tensioner 14 acts to tension the top thread so that the stitch maker 15 can pull against this tension to create the stitch. Similarly, shuttle thread tensioner 24 urges leaf spring 47 on shuttle 40 so as to trap the bottom thread to prevent it from unspooling from bobbin 41.

Once the stitch is formed, shuttle drive arms 23 act in reverse to drive shuttle 40 backwards out of the lumen of graft 5 to make room for needle 12 to drive again into graft 5 and form the next loop. The placement of the second stitch can be chosen so as to form a stitch over the support wire, thereby stitching it to graft 5. This can be achieved by means of needle wobble drive 13 operating on needle 12 so as to achieve fine positioning of needle 12 with respect to the support wire and graft 5.

As the support wire is sewn to graft 5, the position of graft 5 with respect to sew arm 10 is continually adjusted by means of the graft grips, graft bed height drive 6 and graft tilt drive 8.

In an alternative embodiment, shuttle 50 is employed instead of shuttle 40. Thread is wound onto bobbin 41 which is fitted into bobbin carrier 51, and bobbin carrier 51 is seated in recess 54 in shuttle rod 53 as shown in FIG. 4C. Shuttle rod 53 is then moved back and forth in the same manner described above for shuttle 40 in shuttle tube 20. Needle 12 passes through slit 55 and then retracts slightly to form a loop. Shuttle rod 53 then advances further to engage nose 52 in said loop. Stitches are thereafter formed in the same way as above.

Although the invention has been defined in terms of applying thread to a tubular medical implant, which can comprise a graft, a stent, a graft-stent, a graft fixation device, ophthalmic orbital reinforcement devices, annuli for heart valve supports, vein implants, vein valve supports or any other tubular medical form, it will be appreciated that the method and apparatus of the invention can equally be employed to stitch thread to the surface of any tubular form.

It will be appreciated that the parts of apparatus herein described may be operated in order to achieve further objectives not specifically described. For example, the apparatus may be used to form three dimensional textile structures such as artificial tissue structures or substrates to support the same.

The invention claimed is:

1. A method for attaching reinforcement wire to the surface of a medical implant, comprising the steps of:
   a. determining the position at which the wire is to be attached,
   b. locating the wire proximate said position,
   c. employing a needle to move the wire closer to said position, wherein the needle is:
      (1) positioned on the side of the wire opposite to the position at which the wire is to be attached, with the tip of the needle disposed between the plane of the surface and the plane of the tangent of the wire parallel to the plane of the surface, and
      (2) moved towards said position such that it contacts the wire and moves it closer to said position; and
   d. moving the needle substantially perpendicular to the surface to make a stitch therein.

2. A method as claimed in claim 1, wherein the needle is provided on a mechanized sewing machine.

3. A method as claimed in claim 1, wherein:
   a. the steps of claim 1 are cyclically repeated, and
   b. the needle is employed in the second cycle to move the wire closer to the stitch formed in the first cycle, with the thread passing over the wire from the first to the second stitch, thereby attaching the wire to the surface close to or at the said position.

4. A method as claimed in claim 1, wherein the implant is a tubular graft.

5. An apparatus for attaching reinforcement wire to the surface of a medical implant, comprising:
   a. a support for the implant,
   b. a needle to drive a first thread through the implant surface,
   c. a bobbin for carrying a second thread to make a stitch in combination with the first thread,
   c. means for locating the wire proximate to the position at which the wire is to be attached to the implant surface, and
   d. means for determining the level of the implant surface and controlling the height of the needle relative to said level,
   wherein the needle is moveable perpendicular and parallel to the plane of the implant surface, whereby the needle can be employed to move the wire closer to said position before making a stitch.

6. An apparatus as claimed in claim 5, wherein the needle and the bobbin are disposed so that the longitudinal axes thereof lie in a common plane.

7. An apparatus for stitching thread to the wall of a tubular medical implant, comprising:
   a. a support for the implant,
   b. a needle to drive a first thread through the wall and into a bore of the implant, and
   c. a bobbin for carrying a second thread through an open end of the implant into said bore in order to form a stitch in combination with the first thread,
   wherein the needle and the bobbin are disposed so that the longitudinal axes thereof lie in a common plane.

8. An apparatus as claimed in claim 7, wherein an elongate bobbin support is provided to support the bobbin inside the bore of the implant.

9. An apparatus as claimed in claim 7, wherein the bobbin support is a rod having a recess in which the bobbin can be seated.

10. An apparatus as claimed in claim 7, wherein the bobbin support is a runner in which the bobbin is free to move into and out of said bore.

11. An apparatus as claimed in claim 10, in which the runner is in the form of a tube with a slot provided therein to allow the needle access to the bobbin through the slot.

12. An apparatus as claimed in claim 7, in which the bobbin sits in a shuttle.

13. An apparatus as claimed in claim 12, wherein the shuttle is an elongate element with a D-shaped cross section for at least part of its length.

14. An apparatus as claimed in claim 7, additionally comprising means for tensioning the first thread, wherein the means for tensioning operates independently of the mechanism for driving the needle.

15. A method for stitching thread to the wall of a tubular medical implant, comprising the steps of:
   a. driving a first thread through the wall and into a bore of the implant using a needle,
   b. forming a loop of the first thread,
   c. moving a bobbin carrying a second thread trough an open end of the implant into said bore,
   d. passing the second thread through the loop formed in the first thread,
   e. closing said loop in order to form a stitch, and
   f. withdrawing the bobbin from said bore, wherein the bobbin and the needle are disposed so that the longitudinal axes thereof lie in a common plane, and wherein the needle is withdrawn sufficiently before the second thread is passed trough said loop so that the bobbin and the needle do not make contact.

16. A method as claimed in claim 15, wherein said loop is formed in the first thread by beginning to withdraw the needle, but wherein the end of the needle is withdrawn completely from the bore only alter the shuttle has engaged said loop.

17. A method for attaching reinforcement wire to the wall of a tubular medical implant, comprising the steps of:
   a. positioning the wire proximate the intended attachment point,
   b. driving a first thread through the wall and into the bore of the implant using a needle,
   c. forming a loop of the first thread,
   d. moving a bobbin along the longitudinal axis of the implant in order to carry a second thread through the loop formed in the first thread,
   e. closing said loop in order to form a first stitch,
   f. withdrawing the needle from the implant,
   g. moving the needle to a position on the side of the wire opposite to the first stitch, and
   h. repeating the foregoing steps b-e to form a second stitch.

18. A method as claimed in claim 17, additionally comprising the steps of:
   a. determining the position at which die wire is to be attached,
   b. locating the wire proximate said position,
   c. employing a needle to move the wire closer to said position, and
   d. employing said needle to make a stitch in the surface.

19. A method as claimed in claim 17, wherein all of the said steps are carried out under the control of a first program.

20. A method as claimed in claim 17, wherein the method steps are repeated a plurality of times in order to form a plurality of stitches in the implant.

21. A method as claimed in claim 20, wherein the number and position of said plurality of stitches is controlled by means of a second program.

22. A method as claimed in claim 21 wherein the second program can control the first.

23. A method as claimed in claim 21 wherein the first and second programs are in the form of computer software.

24. A method as claimed in claim 17, wherein the needle is employed to deform the wire into a required configuration.

25. A method as claimed in claim 17 wherein said configuration is a zig-zag.

* * * * *